US011713443B2

(12) United States Patent
Rosin et al.

(10) Patent No.: US 11,713,443 B2
(45) Date of Patent: *Aug. 1, 2023

(54) INTEGRATED PROCESS FOR FILTERING CONSTITUENTS FROM A GAS STREAM

(71) Applicant: LanzaTech, Inc., Skokie, IL (US)

(72) Inventors: Richard Rosin, Glencoe, IL (US); Jason Greene, Arlington Heights, IL (US); Taylor Schulz, Chicago, IL (US)

(73) Assignee: LanzaTech, Inc., Skokie, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/817,097

(22) Filed: Aug. 3, 2022

(65) Prior Publication Data
US 2022/0372426 A1 Nov. 24, 2022

Related U.S. Application Data

(63) Continuation of application No. 16/273,865, filed on Feb. 12, 2019, now Pat. No. 11,441,116.

(60) Provisional application No. 62/656,813, filed on Apr. 12, 2018, provisional application No. 62/629,160, filed on Feb. 12, 2018.

(51) Int. Cl.
| | |
|---|---|
| *C12M 1/00* | (2006.01) |
| *C12M 1/34* | (2006.01) |
| *C12P 1/04* | (2006.01) |
| *C01B 3/38* | (2006.01) |

(52) U.S. Cl.
CPC ............ *C12M 43/04* (2013.01); *C01B 3/38* (2013.01); *C12M 21/12* (2013.01); *C12M 29/26* (2013.01); *C12M 41/34* (2013.01); *C12M 47/18* (2013.01); *C12P 1/04* (2013.01); *C01B 2203/043* (2013.01); *C01B 2203/0475* (2013.01); *C01B 2203/0485* (2013.01); *C01B 2210/007* (2013.01); *C01B 2210/0051* (2013.01); *C01B 2210/0064* (2013.01); *C01B 2210/0067* (2013.01)

(58) Field of Classification Search
CPC ...... C12M 43/04; C12M 29/26; C12M 41/34; C12M 21/12; C12M 47/18; C12P 1/04; C01B 3/38; C01B 2210/007; C01B 2203/0485; C01B 2203/0475; C01B 2210/0067; C01B 2210/0064; C01B 2210/0051; C01B 2203/043; C01B 3/12; C01B 3/50; C01B 3/54; C01B 2203/0435; C01B 2203/062; C01B 2203/0045; C01B 2203/0043

See application file for complete search history.

(56) References Cited

U.S. PATENT DOCUMENTS

| | | | |
|---|---|---|---|
| 4,360,504 A | 11/1982 | Blanck | |
| 11,441,116 B2 * | 9/2022 | Rosin | ............ C12M 43/04 |
| 2005/0281725 A1 | 12/2005 | Hague | |
| 2013/0065282 A1 * | 3/2013 | Tran | ............ C12P 7/649 435/161 |
| 2018/0141000 A1 * | 5/2018 | Winter | ............ C10J 3/482 |
| 2018/0250626 A1 * | 9/2018 | Fujimori | ............ B01D 53/81 |
| 2019/0256874 A1 * | 8/2019 | Fujimori | ............ B01D 53/047 |

FOREIGN PATENT DOCUMENTS

| | | | |
|---|---|---|---|
| RU | 2297878 C2 | 4/2007 | |
| WO | 2011002318 A1 | 1/2011 | |
| WO | WO 2011 028 137 A1 * | 3/2011 | ............ C12P 7/065 |
| WO | 2012054798 A3 | 8/2012 | |

OTHER PUBLICATIONS

"Zhou Fu-Xun et al., "Catalytic Deoxygenating Characteristics of Oxygen-Bearing Coal Mine Methane in the Fluidized Bed Reactor", Journal of Fuel Chemistry and Technology, 2013, vol. 41, Issue 5, p. 523-529 abstract, p. 524-528."
Eurasian Search Report, Application No. 202292197, dated Dec. 21, 2022, 2 pages (4 pages with translation).

* cited by examiner

*Primary Examiner* — Timothy C Vanoy

(57) ABSTRACT

The invention provides a process for producing a fermentable gas stream from a gas source that contains one or more constituent which may be harmful to the fermentation process. To produce the fermentable gas stream, the gas stream is passed through a specifically ordered series of removal modules. The removal modules remove and/or convert various constituents found in the gas stream which may have harmful effects on downstream removal modules and/or inhibitory effects on downstream gas fermenting microorganisms. At least a portion of the fermentable gas stream is preferably capable of being passed to a bioreactor, which contains gas fermenting microorganisms, without inhibiting the fermentation process.

20 Claims, 4 Drawing Sheets

INTEGRATED PROCESS FOR FILTERING CONSTITUENTS FROM A GAS STREAM

CROSS-REFERENCE TO RELATED APPLICATIONS

This application is a continuation of U.S. patent application Ser. No. 16/273,865, filed on Feb. 12, 2019, which claims the benefit of U.S. Provisional Patent Application Nos. 62/629,160, filed on Feb. 12, 2018, and 62/656,813, filed on Apr. 12, 2018, the entirety of which are incorporated herein by reference.

FIELD OF THE INVENTION

This invention relates to systems and processes for removing constituents from a gas stream. In particular, the invention relates to the removal of constituents from a gas stream that may be harmful to subsequent removal modules and/or gas fermenting microbes in a downstream process.

BACKGROUND OF THE INVENTION

There is an immediate need to drastically reduce the emissions associated with global fossil fuel consumption in order to limit climate change. However, carbon-based materials, chemicals, and transportation fuels are predominantly made from fossil sources and currently there is no alternative source available to adequately displace them.

Gas fermenting microorganisms that fix carbon dioxide ($CO_2$) and carbon monoxide (CO) can ease the effect of this dependence as they can convert gaseous carbon into useful fuels and chemicals.

Gas fermenting microorganisms can utilize a wide range of feedstocks including gasified organic matter of any sort (i.e. municipal solid waste, industrial waste, biomass, and agricultural waste residues) or industrial off-gases (i.e. from steel mills or other processing plants).

The wide variety of industries producing these gas streams invariably introduce impurities due to process variables and trace elements in process feedstocks. These impurities can affect downstream conversion performance of gas fermenting microbes. For example, mono nitrogenous species such as hydrogen cyanide (HCN), ammonia ($NH_3$), nitrogen oxide ($NO_x$) and other known enzyme inhibiting gases such as acetylene ($C_2H_2$), ethylene ($C_2H_4$), ethane ($C_2H_6$), BTEX (benzene, toluene, ethyl benzene, xylene), and oxygen ($O_2$) can be present. Sulfur compounds in the gas such as hydrogen sulfide ($H_2S$), carbonyl sulfide (COS), carbon disulfide ($CS_2$) can in turn negatively affect catalyst-based scrubbing systems.

For many of the above compounds, commercially available removal systems exist; however, these systems have not been used for microbial gas fermentation. Microbial gas fermentation, as the downstream process, is a relatively new alternative to conventional catalytic conversion technologies and requires relatively specific impurity limitations. To ensure successful, noninhibited gas fermentation, clean-up of these gases must be completed.

There are three central concerns with cleaning gas for gas fermentation, including (1) excessive consumption of the desired reactant compounds for microbial fermentation; (2) reaction to form other undesired compounds which will act as microbial inhibitors; and (3) reduction of the inhibitory compounds in the feed stream to sufficiently low levels to ensure successful, noninhibited gas fermentation.

Accordingly, there remains a need for an invention that strategically cleans up gas streams from industrial or other processes to provide a suitable gas for a downstream fermentation process, while also avoiding the aforementioned concerns.

BRIEF SUMMARY OF THE INVENTION

The invention provides a process for producing a fermentable gas stream from an input gas stream comprising CO, $CO_2$, or $H_2$, or a combination thereof, wherein the process comprises passing the input gas stream to a hydrolysis module, wherein at least one constituent of the gas stream is removed and/or converted to provide a post-hydrolysis gas stream, passing the post-hydrolysis gas stream to an acid gas removal module, wherein at least one further constituent of the gas stream is removed and/or converted to produce an acid gas depleted stream, passing the acid gas depleted stream to a deoxygenation module, wherein at least one further constituent is removed and/or converted to produce a fermentable gas stream. The order of these removal processes is critical to the successful production of a gas stream which is suitable for fermentation.

In at least one embodiment, at least one constituent removed is a microbe inhibitor and/or a catalyst inhibitor.

In particular embodiments, at least one or more of the constituents removed and/or converted by the hydrolysis module is carbonyl sulfide (COS) and/or hydrogen cyanide (HCN).

The constituents removed and/or converted by the acid gas removal module may be selected from the group consisting of carbon dioxide ($CO_2$), hydrogen sulfide ($H_2S$), and hydrogen cyanide (HCN).

In particular embodiments, at least one or more of the constituents removed and/or converted by the deoxygenation module is oxygen ($O_2$) and/or acetylene ($C_2H_2$).

In certain instances, the hydrolysis module is bypassed, and the input gas stream is delivered to the acid gas removal module.

The process may further include a catalytic hydrogenation module. In embodiments utilizing a catalytic hydrogenation module, the acid gas depleted stream is passed to the catalytic hydrogenation module, prior to being passed to the deoxygenation module, wherein at least one constituent from the acid gas depleted stream is removed and/or converted prior to being passed to the deoxygenation module. At least one constituent removed and/or converted by the catalytic hydrogenation module is acetylene ($C_2H_2$).

The process may include at least one additional module selected from the group comprising: particulate removal module, chloride removal module, tar removal module, hydrogen cyanide removal module, additional acid gas removal module, temperature module, and pressure module.

In particular instances, the additional acid gas removal module is a pressure swing adsorption (PSA) module.

In particular embodiments, the process includes monitoring devices for measuring the level of constituents present in the gas stream. The one or more monitoring devices may be placed before and/or after one or more module. In certain instances, the process may be capable of bypassing one or more module as a function of the level of one or more constituent in the gas stream.

The process may include a hydrogen cyanide removal module capable of receiving the post-deoxygenation gas stream. The hydrogen cyanide removal module may remove at least a portion of the hydrogen cyanide from the gas stream prior to passing the gas stream to the bioreactor.

Preferably, the constituent levels are reduced to predetermined levels prior to being passed to the bioreactor, such that the gas stream is fermentable. In particular embodiments, the predetermined level of constituents comprises no more than one hundred parts per million (100 ppm) oxygen ($O_2$), one part per million (1 ppm) hydrogen cyanide (HCN), and one part per million (1 ppm) acetylene ($C_2H_2$). In certain instances, the predetermined level of constituents comprises no more than one hundred parts per billion (100 ppb) hydrogen cyanide (HCN).

The bioreactor may contain a culture comprising a fermentation broth and one or more microorganisms. In particular embodiments, the one or more microorganisms is a carboxydotrophic bacterium.

The process may be capable of sending the treated gas stream to a carbon capture means instead of, or prior to, the treated gas stream being passed to the bioreactor.

The particular embodiments, the process is capable of receiving gas streams from one or more sources. At least a portion of the gas stream may be derived from an industrial source. Additionally, at least a portion of the gas stream may be a synthesis gas. Furthermore, at least a portion of the gas stream may be a producer gas.

In particular embodiments, the invention provides a process for producing a fermentable gas stream, wherein the process comprises treating a gas stream comprising CO, $CO_2$, or $H_2$ in a gas treatment process to remove one or more undesired constituent from the gas stream, wherein the step of treating the gas stream comprises passing the gas stream to a hydrolysis module, wherein at least one constituent of the gas stream is converted to provide a post-hydrolysis stream, passing the post-hydrolysis stream to an acid gas removal module, wherein at least one further constituent of the stream is removed to provide an acid gas depleted stream, and passing the acid gas depleted stream to a deoxygenation module, wherein at least one further constituent is converted to provide a fermentable gas stream.

Preferably, the fermentable gas stream comprises depleted levels of oxygen ($O_2$), hydrogen cyanide (HCN), and acetylene ($C_2H_2$) compared to the input gas stream prior to being passed through the treatment process.

In one embodiment, the fermentable gaseous substrate comprises less than one-hundred parts per million (100 ppm) oxygen ($O_2$).

In one embodiment, the fermentable gaseous substrate comprises less than one part per million (1 ppm) hydrogen cyanide (HCN). Preferably, the fermentable gaseous substrate comprises less than one hundred parts per billion (100 ppb) hydrogen cyanide (HCN).

In one embodiment, the fermentable gaseous substrate comprises less than one part per million (1 ppm) acetylene ($C_2H_2$).

In various embodiments, the process utilizes one or more specialized catalysts to produce a fermentable gas stream from an input gas stream. Preferably, the specialized catalyst is used to reduce the oxygen to less than 100 ppm, acetylene to less than 1 ppm, and the hydrogen cyanide to less than 1 ppm. In certain instances, the specialized catalyst comprises reduced copper metal on a high surface area catalyst such as silica, alumina, titania, ceria, lanthana, silica-alumina, carbon, or many other materials known to those skilled in the art. In certain instances, the specialized catalyst used is copper (I) supported on alumina. In certain instances, the specialized catalyst comprises sulfided copper (I) supported on alumina, such that it is tolerant to sulfur. In certain instances, the specialized catalyst comprises copper (II) supported on alumina. In certain instances, the specialized catalyst comprises sulfided copper (II) supported on alumina, such that it is tolerant to sulfur. Preferably, the specialized catalyst comprises sulfided copper supported on alumina when treating an input gas stream with high sulfur content.

In various embodiments, the process receives an input stream comprising various constituents at various levels. In certain instances, the input gas stream comprises oxygen up to 7000 ppm, acetylene up to 700 ppm, and hydrogen cyanide up to 60 ppm, which may represent a gas received from a steel mill. In certain instances, the input stream comprises oxygen up to 10,000 ppm, acetylene up to 1500 ppm, and hydrogen cyanide up to 500 ppm, which may represent a gas stream from a gasification process (biomass or municipal solid waste) or treated coke oven gas. Preferably, the process consumes less than 10 percent of the carbon monoxide in the input gas stream. The process may, in certain instances, be conducted under pressure. For example, the process may be carried out at a pressure of at least 138 kPag.

At least a portion of the fermentable gas stream may be provided to a bioreactor containing a culture of C1-fixing microorganisms. Preferably, the C1-fixing microorganism is a carboxydotrophic bacterium. The carboxydotrophic bacterium may be selected from the group comprising *Moorella, Clostridium, Ruminococcus, Acetobacterium, Eubacterium, Butyribacterium, Oxobacter, Methanosarcina*, and *Desulfotomaculum*.

Preferably, the carboxydotrophic bacterium is *Clostridium autoethanogenum*.

In certain instances, the industrial source is selected from the group consisting of ferrous metal products manufacturing, such as a steel mill manufacturing, non-ferrous products manufacturing, petroleum refining, coal gasification, electric power production, carbon black production, ammonia production, methanol production, and coke manufacturing.

In certain instances, the synthesis gas source is selected from the group consisting of gasification of coal or refinery residues, gasification of biomass or lignocellulosic material, reforming of natural gas, and gasification of municipal solid waste or industrial solid waste.

DETAILED DESCRIPTION OF THE INVENTION

Figure 1:
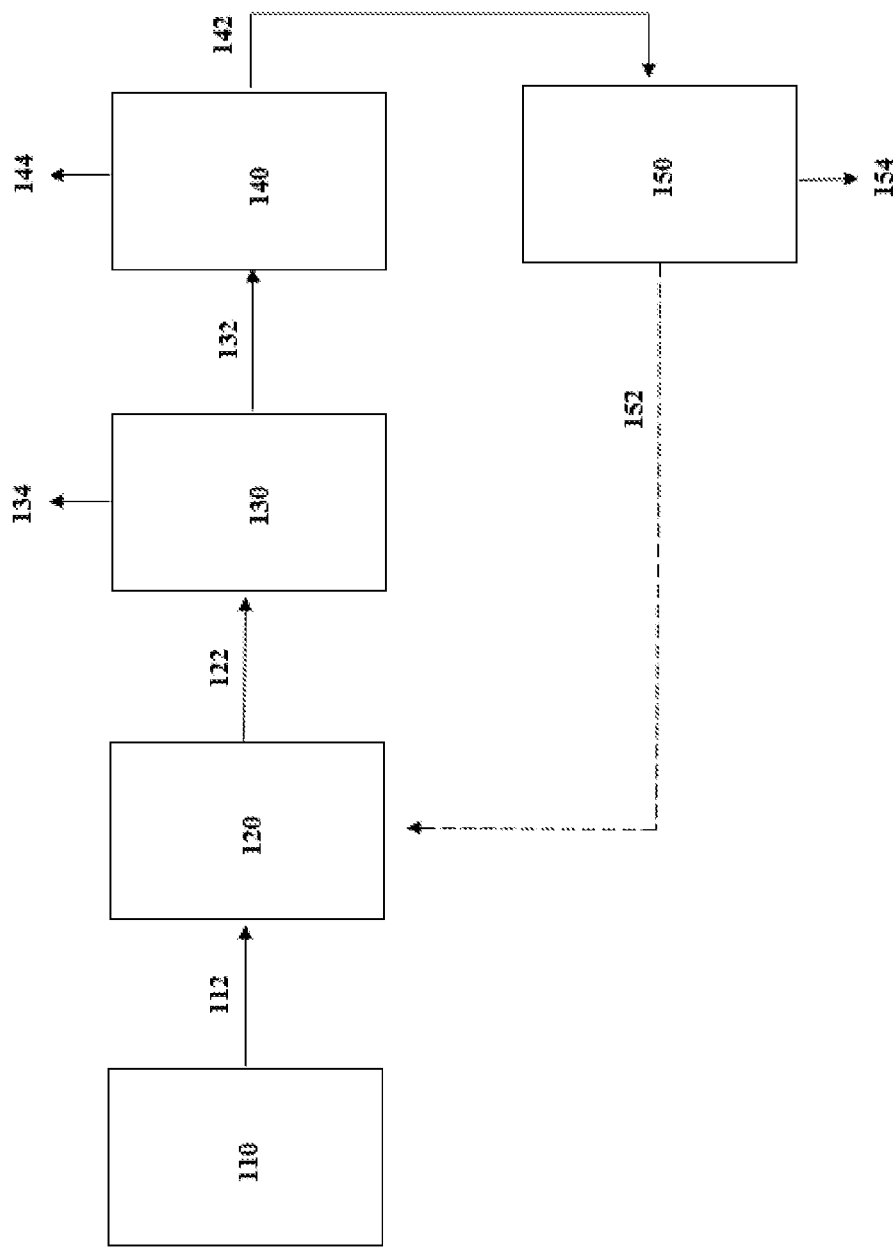
FIG. 1 shows a process integration scheme depicting the integration of a hydrolysis module, an acid gas removal module, and a deoxygenation module.

The inventors have identified that by integrating a series of removal modules certain constituents can be removed from gas that would inhibit the downstream removal modules and/or the downstream fermentation process. Specifically, the inventors have identified a critical order in which to position removal modules to ensure the successful production of a gas stream suitable for fermentation. Furthermore, the inventors found that these modules were effective at removing inhibitory constituents without consuming significant amounts of desired compounds or producing undesired compounds.

Definitions

Unless otherwise defined, the following terms as used throughout this specification are defined as follows:

The term "gasification" and the like should be interpreted as the process that converts organic or fossil fuel-based carbonaceous materials into carbon monoxide (CO), hydrogen ($H_2$), and carbon dioxide ($CO_2$).

The term "syngas" should be interpreted to mean a gas stream typically used in the synthetic production of chemicals.

The term "producer gas" should be interpreted to mean a gas stream typically used as an energy source for generating heat and/or power.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

"Gaseous substrates comprising carbon monoxide", "gas stream comprising carbon monoxide" and the like, when used in herein include any gas which contains carbon monoxide. The gas stream will typically contain a significant proportion of CO, preferably at least about 5% to about 100% CO by volume.

While it is not necessary for the substrate to contain any hydrogen, the presence of $H_2$ should not be detrimental to product and/or by-product formation in accordance with methods of the invention. In particular embodiments, the presence of hydrogen results in improved overall efficiency of alcohol production. For example, in particular embodiments, the gas stream may comprise an approx. 2:1, or 1:1, or 1:2 ratio of $H_2$:CO. In one embodiment, the gas stream comprises about 30% or less $H_2$ by volume, 20% or less $H_2$ by volume, about 15% or less $H_2$ by volume or about 10% or less $H_2$ by volume. In other embodiments, the gas stream comprises low concentrations of $H_2$, for example, less than 5%, or less than 4%, or less than 3%, or less than 2%, or less than 1%, or is substantially hydrogen free. The gas stream may also contain some $CO_2$ for example, such as about 1% to about 80% $CO_2$ by volume, or 1% to about 30% $CO_2$ by volume. In one embodiment, the gas stream comprises less than or equal to about 20% $CO_2$ by volume. In particular embodiments, the gas stream comprises less than or equal to about 15% $CO_2$ by volume, less than or equal to about 10% $CO_2$ by volume, less than or equal to about 5% $CO_2$ by volume or substantially no $CO_2$.

"Gas stream" refers to any stream of substrate which is capable of being passed, for example, from one module to another, from one module to a bioreactor, and/or from one module to a carbon capture means.

"Reactants" as used herein refer to a substance that takes part in and undergoes change during a chemical reaction. In particular embodiments, the reactants include, but are not limited to, CO and/or $H_2$.

"Microbe inhibitors" as used herein refer to one or more constituent that slows down or prevents a particular chemical reaction or other process including microbial fermentation. In particular embodiments, the microbe inhibitors include, but are not limited to, Oxygen ($O_2$), hydrogen cyanide (HCN), acetylene ($C_2H_2$), and BTEX (benzene, toluene, ethyl benzene, xylene).

"Catalyst inhibitor", "adsorbent inhibitor", and the like, as used herein, refer to one or more substance that decreases the rate of, or prevents, a desired chemical reaction. In particular embodiments, the catalyst and/or adsorbent inhibitors may include but are not limited to, hydrogen sulfide ($H_2S$) and carbonyl sulfide (COS).

"Removal module", "clean-up module", "processing module" and the like, includes technologies that are capable of either converting and/or removing microbe inhibitors and/or catalyst inhibitors from the gas stream.

The term "constituents", "contaminants", and the like, as used herein, refers to the reactants, microbe inhibitors, and/or catalyst inhibitors that may be found in the gas stream.

The term "treated gas" refers to the gas stream that has been passed through at least one removal module and has had one or more constituent removed and/or converted.

The term "predetermined level", "predetermined level of constituents", and the like, as used herein, refer to the amount of one or more constituent deemed to be acceptable in the gas stream. The predetermined levels stated herein were identified by performing microbial tolerance experiments.

The term "fermentable gaseous substrate", "fermentable gas stream" and the like, as used herein, refers to a gas stream that contains a predetermined level of constituents, and is capable of being used as a carbon source by C1-fixing microorganisms.

The term "carbon capture" as used herein refers to the sequestration of carbon compounds including $CO_2$ and/or CO from a stream comprising $CO_2$ and/or CO and either:
  converting the $CO_2$ and/or CO into products; or
  converting the $CO_2$ and/or CO into substances suitable for long term storage; or
  trapping the $CO_2$ and/or CO in substances suitable for long term storage;
  or a combination of these processes.

The term "bioreactor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Bubble Column, Gas Lift Fermenter, Static Mixer, a circulated loop reactor, a membrane reactor, such as a Hollow Fibre Membrane Bioreactor (HFM BR) or other vessel or other device suitable for gas-liquid contact. The reactor is preferably adapted to receive a fermentable gas stream comprising CO or $CO_2$ or $H_2$ or mixtures thereof. The reactor may comprise multiple reactors (stages), either in parallel or in series. For example, the reactor may comprise a first growth reactor in which the bacteria are cultured and a second fermentation reactor, to which fermentation broth from the growth reactor may be fed and in which most of the fermentation products may be produced.

"Nutrient media" or "Nutrient medium" is used to describe bacterial growth media. Generally, this term refers to a media containing nutrients and other components appropriate for the growth of a microbial culture. The term "nutrient" includes any substance that may be utilized in a metabolic pathway of a microorganism. Exemplary nutrients include potassium, B vitamins, trace metals, and amino acids.

The term "fermentation broth" or "broth" is intended to encompass the mixture of components including nutrient media and a culture or one or more microorganisms. It should be noted that the term microorganism and the term bacteria are used interchangeably throughout the document.

The term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. In addition, the term "acetate" includes both acetate salt alone and a mixture of molecular or free acetic acid and acetate salt, such as the mixture of acetate salt and free acetic acid present in a fermentation broth as described herein.

The term "acid gas" as used herein is a classification of gas which contains mixtures of constituents in quantities making the gas acidic. Acid gas may contain large proportions of hydrogen sulfide ($H_2S$) and/or carbon dioxide ($CO_2$). Additionally, the acid gas may contain proportions of carbonyl sulfide (COS), hydrogen chloride (HCl), hydrogen fluoride (HF), and/or hydrogen cyanide (HCN).

The term "desired composition" is used to refer to the desired level and types of components in a substance, such as, for example, of a gas stream. More particularly, a gas is considered to have a "desired composition" if it contains a particular component (i.e. CO and/or $CO_2$) and/or contains a particular component at a particular level and/or does not contain a particular component (i.e. a contaminant harmful to the microorganisms) and/or does not contain a particular component at a particular level. More than one component may be considered when determining whether a gas stream has a desired composition. Preferably, the gas stream being sent to the bioreactor is fermentable, such that it has a desired composition.

Unless the context requires otherwise, the phrases "fermenting", "fermentation process" or "fermentation reaction" and the like, as used herein, are intended to encompass both the growth phase and product biosynthesis phase of the gaseous substrate.

A "microorganism" is a microscopic organism, especially a bacterium, archea, virus, or fungus. The microorganism of the invention is typically a bacterium. As used herein, recitation of "microorganism" should be taken to encompass "bacterium."

A "parental microorganism" is a microorganism used to generate a microorganism of the invention. The parental microorganism may be a naturally-occurring microorganism (i.e., a wild-type microorganism) or a microorganism that has been previously modified (i.e., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. The microorganism of the invention may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In a preferred embodiment, the parental microorganism is *Clostridium autoethanogenum* LZ1561, which was deposited on Jun. 7, 2010, with Deutsche Sammlung von Mikroorganismen and Zellkulturen GmbH (DSMZ) located at Inhoffenstraße 7B, D-38124 Braunschweig, Germany on Jun. 7, 2010, under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (i.e., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a parental microorganism. In one embodiment, the microorganism of the invention is derived from *Clostridium autoethanogenum*, *Clostridium ljungdahlii*, or *Clostridium ragsdalei*. In a preferred embodiment, the microorganism of the invention is derived from *Clostridium autoethanogenum* LZ1561, which is deposited under DSMZ accession number DSM23693.

"Wood-Ljungdahl" refers to the Wood-Ljungdahl pathway of carbon fixation as described, i.e., by Ragsdale, *Biochim Biophys Acta*, 1784: 1873-1898, 2008. "Wood-Ljungdahl microorganisms" refers, predictably, to microorganisms containing the Wood-Ljungdahl pathway. Generally, the microorganism of the invention contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (i.e., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium.

An "anaerobe" is a microorganism that does not require oxygen for growth. An anaerobe may react negatively or even die if oxygen is present above a certain threshold. However, some anaerobes are capable of tolerating low levels of oxygen (i.e., 0.000001-5% oxygen). Typically, the microorganism of the invention is an anaerobe.

"Acetogens" are obligately anaerobic bacteria that use the Wood-Ljungdahl pathway as their main mechanism for energy conservation and for the synthesis of acetyl-CoA and acetyl-CoA-derived products, such as acetate (Ragsdale, *Biochim Biophys Acta*, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, N.Y., 2006). All naturally occurring acetogens are C1-fixing, anaerobic, autotrophic, and non-methanotrophic. Typically, the microorganism of the invention is an acetogen.

An "ethanologen" is a microorganism that produces or is capable of producing ethanol. Typically, the microorganism of the invention is an ethanologen.

An "autotroph" is a microorganism capable of growing in the absence of organic carbon. Instead, autotrophs use inorganic carbon sources, such as CO and/or $CO_2$. Typically, the microorganism of the invention is an autotroph.

A "carboxydotroph" is a microorganism capable of utilizing CO as a sole source of carbon and energy. Typically, the microorganism of the invention is a carboxydotroph.

A "methanotroph" is a microorganism capable of utilizing methane as a sole source of carbon and energy. In certain embodiments, the microorganism of the invention is a methanotroph or is derived from a methanotroph. In other embodiments, the microorganism of the invention is not a methanotroph or is not derived from a methanotroph.

"Substrate" refers to a carbon and/or energy source for the microorganism of the invention. Typically, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons.

The term "co-substrate" refers to a substance that, while not necessarily being the primary energy and material source for product synthesis, can be utilized for product synthesis when added to another substrate, such as the primary substrate.

The substrate and/or C1-carbon source may be a waste gas obtained as a by-product of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be derived from a number of sources, for example, from industrial processes, including gas emissions from carbohydrate fermentation, gas fermentation, gas emissions from cement making, pulp and paper making, steel making, oil refining and associated processes, petrochemical production, coke production, anaerobic or aerobic digestion, producer gas typically used in heat and/or power generation, synthesis gas (derived from sources including but not limited to biomass, liquid waste streams, solid waste streams, municipal streams, fossil resources including natural gas, coal and oil), natural gas extraction, oil extraction, metallurgical processes, for production and/or refinement of aluminum, copper, and/or ferroalloys, geological reservoirs and catalytic processes (derived from steam sources including but not limited to steam methane reforming, steam naphtha reforming, petroleum coke gasification, catalyst regeneration—fluid catalyst cracking, catalyst regeneration-naphtha reforming, and dry methane reforming). In certain instances, the substrate and/or C1-carbon source may be derived from a combination of two or more sources.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, microbial inhibitors, or dust particles, and/or increase the concentration of desirable components.

In certain embodiments, the fermentation is performed in the absence of carbohydrate substrates, such as sugar, starch, lignin, cellulose, or hemicellulose.

The microorganism of the invention may be cultured with the gas stream to produce one or more products. For instance, the microorganism of the invention may produce or may be engineered to produce ethanol (WO 2007/117157), acetate (WO 2007/117157), butanol (WO 2008/115080 and WO 2012/053905), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene (WO 2013/180584), fatty acids (WO 2013/191567), 2-butanol (WO 2013/185123), 1,2-propanediol (WO 2014/036152), 1-propanol (WO 2014/0369152), chorismate-derived products (WO 2016/191625), 3-hydroxybutyrate (WO 2017/066498), and 1,3-butanediol (WO 2017/066498). In addition to one or more target products, the microorganism of the invention may also produce ethanol, acetate, and/or 2,3-butanediol. In certain embodiments, microbial biomass itself may be considered a product. One or more of these products may be further converted to produce at least one component of diesel, jet fuel, and/or gasoline.

A "native product" is a product produced by a genetically unmodified microorganism. For example, ethanol, acetate, and 2,3-butanediol are native products of *Clostridium autoethanogenum*, *Clostridium ljungdahlii*, and *Clostridium ragsdalei*. A "non-native product" is a product that is produced by a genetically modified microorganism, but is not produced by a genetically unmodified microorganism from which the genetically modified microorganism is derived.

"Selectivity" refers to the ratio of the production of a target product to the production of all fermentation products produced by a microorganism. The microorganism of the invention may be engineered to produce products at a certain selectivity or at a minimum selectivity. In one embodiment, a target product accounts for at least about 5%, 10%, 15%, 20%, 30%, 50%, or 75% of all fermentation products produced by the microorganism of the invention. In one embodiment, the target product accounts for at least 10% of all fermentation products produced by the microorganism of the invention, such that the microorganism of the invention has a selectivity for the target product of at least 10%. In another embodiment, the target product accounts for at least 30% of all fermentation products produced by the microorganism of the invention, such that the microorganism of the invention has a selectivity for the target product of at least 30%.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and the product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for the production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time, in turn, dictates the required volume of a bioreactor, the use of pressurized systems can greatly reduce the volume of the bioreactor required, and consequently the capital cost of the fermentation equipment.

Target products may be separated or purified from a fermentation broth using any method or combination of methods known in the art, including, for example, fractional distillation, vacuum distillation, evaporation, pervaporation, gas stripping, phase separation, and extractive fermentation, including, for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor.

Description

The inventors have surprisingly found that by incorporating various modules together, in a precise order, various gas constituents may be converted and/or removed from the gas stream, in a step-wise manner, where if constituents may be harmful to downstream modules they are removed and/or converted upstream from those modules, which then allows for subsequent removal of other gas constituents, and later feeding of a fermentable gas stream to a bioreactor where the gas may be processed by gas fermenting microorganisms to create useful products. The conversion and/or removal of these constituents is achieved without consuming desired compounds and without creating other undesired compounds. In particular embodiments, the fermentable gas stream may be passed to a carbon capture means for storage.

In particular embodiments, the gas stream is passed, in series, to the following modules for processing: (1) hydrolysis; (2) acid gas removal; (3) catalytic hydrogenation; and (4) deoxygenation. The order in which the gas is passed is critical to the successful production of a fermentable gas stream. Each module is utilized to remove and/or convert one or more constituent in the gas stream.

Hydrolysis Module

Hydrogen cyanide (HCN) and carbonyl sulfide (COS) are two anticipated constituents that first require chemical reaction with water in advance of being successfully removed from the gas stream. The inventors have found that in applications where a high sulfur gas stream is utilized, converting COS to hydrogen sulfide ($H_2S$) may be necessary because many commercial processes cannot efficiently remove sulfur in the form of COS. This conversion occurs according to the following reaction:

$$COS + H_2O \leftrightarrow H_2S + CO_2$$

This conversion can be achieved using any technology capable of converting COS to $H_2S$. In various embodiments, the hydrolysis module utilizes a metal oxide catalyst to perform the conversion. In particular embodiments, an alumina catalyst is used to perform the conversion.

In particular embodiments, the hydrolysis step may include a multibed approach to convert COS and remove $H_2S$. In particular embodiments, the first bed utilizes a conversion bed whereby COS is converted to $H_2S$. An example of such a conversion bed includes the BASF SELEXSORB™ COS. In particular embodiments, the second bed utilizes an iron-based adsorbent, such as the high-capacity non-hazardous granular media sold under the tradename "AxTrap 4001", which removes $H_2S$.

In particular embodiments, the gas stream is fed to the hydrolysis module in order to convert and/or remove one or more constituent from the gas stream. In certain instances, the post-hydrolysis gas stream is depleted in at least one constituent selected from the group comprising: COS and/or HCN.

Acid Gas Removal Module

Acid gas removal refers to a process by which hydrogen sulfide ($H_2S$) and/or carbon dioxide ($CO_2$), as well as other acid gases, are separated from the gas stream.

In certain instances, the acid gas removal module utilizes a zinc oxide (ZnO) catalyst to remove hydrogen sulfide ($H_2S$) from the gas stream.

In particular embodiments, Pressure Swing Adsorption (PSA) is utilized as the acid gas removal module. In particular embodiments, Pressure Swing Adsorption will not reduce each constituent level to desired levels and thus subsequent steps may be necessary. In particular embodiments, a hydrocarbon removal bed is utilized before Pressure Swing Adsorption to remove one or more constituents, including BTEX.

Pressure Swing Adsorption is an adiabatic process which may be used for the purification of gases to remove accompanying impurities by adsorption through suitable adsorbents in fixed beds contained in vessels under high pressure. Regeneration of adsorbents is accomplished by counter current depressurization and by purging at low pressure with previously recovered treated gas. To obtain a continuous flow of product, preferably at least two adsorbers are provided such that at least one adsorber is receiving, treating, and sending a treated gas stream to further treatment modules, and at least one adsorber is used to perform the regeneration of the one or more adsorbers that send the treated gas stream to further treatment modules. Common adsorbents may readily be selected by one of skill in the art dependent on the type of impurity to be absorbed and removed. Suitable adsorbents include zeolitic molecular sieves, activated carbon, silica gel or activated alumina. Combinations of absorbent beds may be used on top of one another, thereby dividing the adsorber contents into a number of distinct zones. Pressure Swing Adsorption involves a pendulating swing in parameters such as pressure, temperature, flow and composition of gaseous and adsorbed phase. Purification or separation of gases using PSA normally takes place at near ambient feed gas temperatures, whereby the components to be removed are selectively adsorbed. Adsorption should ideally be sufficiently reversible to enable regeneration of adsorbents at similar ambient temperature. Additionally, adsorption should preferably be conducted such that the production of undesirable compounds is avoided, or at least minimized.

In embodiments utilizing subsequent steps for acid gas removal, a carbon dioxide adsorption module, or additional acid gas removal module, may be used after the PSA module. The carbon dioxide adsorption module is used to remove carbon dioxide ($CO_2$) from the treated stream in order to bring the carbon dioxide levels within the desired range. In these embodiments, the treated gas from the PSA module may be sent to the carbon dioxide adsorption module prior to being sent to the catalytic hydrogenation module. In embodiments that bypass the catalytic hydrogenation module, or embodiments that do not include a catalytic hydrogenation module, the treated gas from the PSA module may be sent directly to the deoxygenation module.

In particular embodiments, the gas stream is fed to the acid gas removal module in order to convert and/or remove one or more constituent from the gas stream. In certain instances, the acid gas-depleted stream is depleted in at least one constituent selected from the group comprising: carbon dioxide ($CO_2$), hydrogen sulfide ($H_2S$), and hydrogen cyanide (HCN).

Catalytic Hydrogenation Module

Acetylene ($C_2H_2$) acts as a microbe inhibitor. To remove acetylene a catalytic hydrogenation module may be utilized. Catalytic hydrogenation is treatment with hydrogen in the presence of a catalyst such as, but not limited to, nickel, palladium, or platinum. There is not one universal catalyst suitable for the hydrogenation of acetylene. The choice of catalyst greatly depends upon the gas composition and operating conditions. In particular embodiments, palladium is used as the catalyst. In particular embodiments, palladium on alumina ($Pd/Al_2O_3$) is used as the catalyst. An example of such a catalyst is the BASF™ R 0-20/47.

Inhibitors reduce the activity of palladium. Sulfur compounds represent potential palladium inhibitors. Compounds such as hydrogen sulfide ($H_2S$) or carbonyl sulfide (COS) adsorb on palladium and may alter the reaction sites. In particular embodiments, known palladium inhibitors are removed and/or converted prior to catalytic hydrogenation.

In particular embodiments, a catalytic hydrogenation module may be unnecessary for acetylene removal. In addition to being removed by a catalytic hydrogenation module, acetylene may be removed from the gas stream by certain deoxygenation modules. In particular embodiments where the catalytic hydrogenation module is unnecessary, the catalytic hydrogenation module may be bypassed and/or not included in the process. An example of when the catalytic hydrogenation module is unnecessary is when acetylene levels are low enough such that they can be effectively removed via the other modules. In particular embodiments where the acetylene levels are low enough, the gas stream may be passed from the acid gas removal module to the deoxygenation module, bypassing the catalytic hydrogenation module.

In particular embodiments, the gas stream is fed to the catalytic hydrogenation module in order to convert and/or remove one or more constituent from the gas stream. In certain instances, the post-hydrogenation stream is depleted in at least acetylene ($C_2H_2$).

Deoxygenation Module

Oxygen ($O_2$) is a microbe inhibitor. Therefore, the oxygen in the gas stream needs to be reduced to acceptable levels. To reduce the levels of oxygen in the gas stream a deoxygenation module may be utilized. The reduction of oxygen levels may be achieved through any suitable means. In particular embodiments, the deoxygenation module utilizes a catalytic process whereby oxygen ($O_2$) is reduced to either carbon dioxide ($CO_2$) or water ($H_2O$). In particular embodiments, the catalyst used in the deoxygenation module is copper-containing. An example of a such a catalyst is the BASF PURISTAR™ R 3.15 or BASF CU 0226S.

In particular embodiments, the deoxygenation module can be used to effectively reduce the level of acetylene in the gas stream thereby allowing for the catalytic hydrogenation step to be bypassed. One notable difference between the removal of acetylene by the catalytic hydrogenation module and the deoxygenation module is the production of ethane ($C_2H_6$). Removal of acetylene by the deoxygenation module produces higher amounts of ethane than the removal of acetylene by the catalytic hydrogenation module. However, due to the robust nature of the microbe used in the gas fermentation process, the inventors found that the level of ethane produced by the deoxygenation module was not harmful to the microbe, and thus, in particular embodiments, the catalytic hydrogenation module was able to be bypassed.

Another notable difference between the catalytic hydrogenation module and the deoxygenation module is the production of methanol ($CH_3OH$). Methanol may be produced when utilizing any copper-based deoxygenation module. In instances where a copper-based deoxygenation module is utilized to remove acetylene, the removal process produces higher amounts of methanol relative to a removal process utilizing a catalytic hydrogenation module. However, due to the robust nature of the microbe used in the subsequent gas fermentation process, the inventors found that the level of methanol produced by the deoxygenation module was not harmful to the microbe, and thus, in particular embodiments, the catalytic hydrogenation module was able to be bypassed.

In addition to the aforementioned constituents, certain deoxygenation modules may be used to effectively reduce mercury (Hg). Not all gas streams will contain mercury (Hg). However, the treatment process is designed to effectively treat gas streams from a number of sources, some of which may contain mercury (Hg). Therefore, in certain instances where the gas stream contains mercury (Hg), a deoxygenation module may be utilized to effectively remove mercury (Hg) from the gas stream. When mercury (Hg) is removed from the gas stream by the deoxygenation module, the post-deoxygenation stream may be depleted in mercury (Hg).

In particular embodiments, the gas stream is fed to the deoxygenation module in order to convert and/or remove one or more constituent from the gas stream. In certain instances, the post-deoxygenation stream is depleted in at least oxygen ($O_2$) and/or acetylene ($C_2H_2$). In various instances, the post-deoxygenation stream is depleted in mercury (Hg) in addition to oxygen ($O_2$) and/or acetylene ($C_2H_2$).

Gas Sampling and Analytical System

To manage, maintain, and optimize the process, a robust analytical monitoring and control technology may be necessary. Such instruments may include, but are not limited to, a gas sampling system, and data logging/reporting software tools.

The analysis of the gas stream composition is a critical element of gas treatment. The analysis of the gas stream provides for the measurement and determination of which constituents need to be either converted and/or removed from the gas stream. To ensure that the gas stream has a desired composition, measurement of constituents in the gas stream at numerous points may be necessary. These measurements may be achieved through any suitable means, which may include online automatic monitoring, and may be completed in either a continuous and/or a periodic manner. In particular embodiments, the gas stream may be measured before and/or after being passed to the different removal modules.

In particular embodiments, the gas stream is measured prior to being passed to one or more removal modules. In certain instances, the measurement of the constituents present in the gas stream prior to being passed to the one or more removal modules determines which removal modules will be utilized. In particular embodiments, the determination of whether or not to utilize a hydrolysis module is dependent on, at least in part, the measurement of the carbonyl sulfide (COS) present in the gas stream. In particular embodiments, the determination of whether or not to utilize a catalytic hydrogenation module is dependent on, at least in part, the measurement of the acetylene ($C_2H_2$) present in the gas stream. In particular embodiments, the determination of whether or not to utilize a hydrogen cyanide removal module is dependent on, at least in part, the measurement of the hydrogen cyanide (HCN) present in the gas stream.

The constituents present in the gas stream may vary based upon numerous factors. In certain embodiments, the constituents present in the gas stream are variable based upon the source from which the gas stream is derived. For example, gas streams sourced from a gasification process may have differing levels of constituents based upon changes in the substance being fed to the gasifier. In certain embodiments, the constituents present in the gas stream are variable based upon the gasifier operations. For example, gas streams sourced from gasification processes may have differing levels of constituents when plugging occurs in the gasifier.

In particular instances, the gas stream is obtained from a mixture of two or more sources. In various embodiments, the composition of the gas stream may be measured prior to, during, and/or after the sources are mixed.

In particular instances, the gas stream may be treated prior to, during, and/or after the sources are mixed. In certain instances, the composition of the gas stream is measured so as to analyze and determine which removal modules are necessary. This determination may be based on, at least in part, the one or more constituents present in the gas stream. In at least one instance, the composition of these gases may fluctuate over time resulting in varying proportions of constituents. These fluctuations may affect the performance of the treatment process. As such, it may be necessary to adjust the treatment process in response to the change in the composition. In various instances, this adjustment of the treatment process includes, the removal, bypassing, and/or addition of one or more removal module. The selection of which removal module to remove, bypass, and/or add may be due at least in part on the particular constituent present. In certain instances, one or more constituent previously not present, or present but below detection levels, may later be measured, which may then necessitate the addition of one or more removal module. In certain instances, increased proportions of carbonyl sulfide (COS) and/or hydrogen cyanide (HCN) may necessitate the addition of a hydrolysis module, whereas decreased proportions of carbonyl sulfide (COS) and/or hydrogen cyanide (HCN) may allow for the removal of the hydrolysis module. In certain instances, increased proportions of carbon dioxide ($CO_2$), hydrogen sulfide ($H_2S$), and/or hydrogen cyanide (HCN) may necessitate the addition of an acid gas removal module, whereas decreased proportions of carbon dioxide ($CO_2$), hydrogen sulfide ($H_2S$), and/or hydrogen cyanide (HCN) may allow for the removal of the acid gas removal module. In certain instances, increased proportions of acetylene ($C_2H_2$) may necessitate the addition of a catalytic hydrogenation module, whereas decreased proportions of acetylene ($C_2H_2$) may allow for the removal of the catalytic hydrogenation module. In certain instances, increased proportions of oxygen ($O_2$) and/or acetylene ($C_2H_2$) may necessitate the addition of a deoxygenation module, whereas decreased proportions of oxygen ($O_2$) and/or acetylene ($C_2H_2$) may allow for the removal of the deoxygenation module.

For online measurement, each measurement point may be connected to the steel tubing to facilitate the transmission of the gas stream through the monitoring device. In particular embodiments, the gas stream is regulated by a pump device to provide a pressurized gas stream to the measurement device. In particular embodiments, the gas stream is pressurized between twenty and thirty pounds per square inch (138-207 kPa). In particular embodiments, different measurement devices are used to measure different constituents.

In particular embodiments, the level of the $C_2H_2$ and HCN levels in the gas stream is monitored by a spectrometer. In certain instances, the spectrometer will monitor the level of one or more of $NH_3$, $CO_2$, and/or $H_2S$ in addition to $C_2H_2$ and/or HCN. In particular embodiments, the spectrometer is configured to measure at various sample points in periodic increments.

In particular embodiments, the hydrocarbons, BTEX, naphthalene, and the oxygenates dimethyl ether, diethyl ether, acetaldehyde, tetrahydrofuran, methyl ethyl ketone, acetone, methanol, and ethanol are measured by a gas chromatograph. In particular embodiments, the chromatograph is configured to measure at various sample points in periodic increments.

In particular embodiments, the nitrogen and sulfur in the gas stream are measured by a device which includes oxidative pyrolysis with Ultraviolet Fluorescence (UVF), and Chemiluminescence technologies. In particular embodiments, the device is configured to measure at various sample points in periodic increments.

In particular embodiments, bulk and/or trace constituents in the gas stream are measured by a gas chromatograph. Bulk and/or trace constituents may include but are not limited to, hydrogen, nitrogen, oxygen, methane, carbon monoxide, carbon dioxide, and hydrogen sulfide. In particular embodiments, the device is configured to measure at various sample points in periodic increments.

In particular embodiments, the various measurement devices may be connected to a software application, whereby the data collected by the measurement devices is interpreted and stored in a database. In particular embodiments, the data is parsed into an easily interpretable format, for example, a spreadsheet.

Specialized Catalyst

The inventors surprisingly found that by utilizing only a specialized catalyst, comprising copper supported on alumina, a fermentable gas stream can be successfully produced from various gas sources. Such gas may be derived, in whole or in part from the combination of gas from one or more industrial process, synthesis gas, and/or producer gas. Specifically, it was found that this specialized catalyst was able to reduce oxygen, acetylene, and hydrogen cyanide such that oxygen is less than 100 ppm, acetylene is less than 1 ppm, and hydrogen cyanide is less than 1 ppm in the fermentable gas stream. In various instances, the copper used for this catalyst was copper (I). In various instances, the copper used for this catalyst was reduced copper.

To treat an input gas with high sulfur content, the inventors found successful production of a fermentable gas stream by utilizing a sulfided version of the specialized catalyst. This sulfidation was achieved by passing a gas comprising a sulfidation reagent over a reduced version of the specialized catalyst. Such reduction and sulfidation can be carried out according to the prior art. In one embodiment, the sulfidation produced a sulfided copper (I) supported on alumina catalyst. In one embodiment, the sulfidation produced a sulfided copper (II) supported on alumina catalyst. The sulfided copper catalyst maybe especially useful at reducing the level of mercury (Hg) when present in the gas stream as coper sulfide is known to be an effective mercury adsorbent.

General

In particular embodiments, the fermentable gas stream is fed to a bioreactor containing C1-fixing microorganisms. These C1-fixing microorganisms are capable of converting the C1-containing gas stream into useful chemicals and products through gas fermentation. To provide a noninhibiting fermentable gas stream to the bioreactor, the gas stream needs to contain a predetermined level of constituents. In particular embodiments, the constituents of concern include oxygen ($O_2$), hydrogen cyanide (HCN), acetylene ($C_2H_2$), BTEX (benzene, toluene, ethyl benzene, xylene), and sulfur ($H_2S$ and COS). In various embodiments, the oxygen ($O_2$) level needs to be below one-hundred parts per million (100 ppm) to be at the predetermined level. In various embodiments, the hydrogen cyanide (HCN) needs to be below one part per million (1 ppm) to be at the predetermined level. Preferably, the hydrogen cyanide (HCN) is below one hundred parts per billion (100 ppb) to be at the predetermined level. In various embodiments, the acetylene ($C_2H_2$) needs to be below one part per million (1 ppm) to be at the predetermined level. In various embodiments, the BTEX needs to be below thirty parts per million (30 ppm) to be at the predetermined level. In various embodiments, the sulfur ($H_2S$ and COS) needs to be below one part per million (1 ppm) to be at the predetermined level. In particular embodiments, all constituents must be at their predetermined levels in order to constitute a predetermined level of constituents.

The system may include further modules both prior to the hydrolysis module and after the deoxygenation module. These further modules may include but are not limited to, a particulate removal module, a chloride removal module, a tar removal module, a hydrogen cyanide removal module, and an additional acid gas removal module, which may remove organics. In certain instances, a module consisting of activated carbon is utilized to remove undesirable organic compounds. These organic compounds may, in certain instances, be formed by one or more removal module. In particular embodiments, the gas is fed into the system to the modules in the following sequence: (1) particulate removal module, (2) chloride removal module, (3) tar removal module, (4) hydrolysis module, (5) acid gas removal module, (5) catalytic hydrogenation module, (6) deoxygenation module, (7) hydrogen cyanide removal module, and (8) additional acid gas removal module.

The particulate removal module may comprise any suitable module capable of removing particulates from the gas stream. Particulates are typically associated with line plugging. In order to avoid line plugging, a particulate removal module may be utilized. In particular embodiments, the particulate removal module is a baghouse. The baghouse may be of any suitable type including, but not limited to, mechanical shakers, reverse gas, and pulse jet. In certain embodiments, the particulate removal module is used prior to the other modules.

The chloride removal module may comprise any suitable module capable of removing chloride from the gas stream. Chloride is typically associated with corrosion in gas cleanup processes. In order to avoid corrosion, a chloride removal module may be utilized. In particular embodiments, the chloride removal module is a caustic scrubber capable of removing hydrogen chloride (HCl). In particular embodiments, the chloride removal module is a cyclone capable of removing ammonium chloride ($NH_4Cl$).

The tar removal module may comprise any suitable module capable of removing tar from the gas stream. Tar may include but is not limited to, a heavy hydrocarbon such as naphthalene, which is typically associated with line plugging. In order to avoid line plugging, a tar removal module may be utilized. In particular embodiments, the tar removal module is an adsorption device. In certain instances, the adsorption device comprises activated carbon.

The hydrogen cyanide removal module may comprise any suitable module capable of removing hydrogen cyanide from the gas stream. Hydrogen cyanide is typically associated with inhibiting microbes. In order to avoid microbe inhibition, a hydrogen cyanide removal module may be utilized. In particular embodiments, the hydrogen cyanide removal module is a copper treated activated carbon device.

The additional acid gas removal module may comprise any suitable module capable of removing carbon dioxide from the gas stream. High levels of carbon dioxide may dilute the gas stream, thus requiring larger bioreactors and/or additional fermentation trains. In order to avoid gas stream dilution by the carbon dioxide, an additional acid gas removal module may be utilized. In particular embodiments, the additional acid gas removal module is a PSA module, which may utilize calcium hydroxide.

The system may include one or more temperature modules to either increase or decrease the temperature of the gas stream. These temperature modules may be placed before and/or after other modules so as to increase or decrease the temperature of the gas stream between modules. The temperature modules may comprise any suitable module capable of increasing or decreasing the temperature of the gas stream. In particular embodiments, the temperature modules are a shell and tube heat exchanger. The shell tube heat exchanger comprises a shell with a bundle of tubes inside the shell. The shell and tube heat exchanger is capable of regulating the temperature of the gas stream by passing a fluid, for example water, through the shell, while simultaneously passing the gas stream through the bundle of tubes. The heat is transferred between the gas stream and the fluid through the tube walls.

The system may include pressure modules to either increase or decrease the pressure of the gas stream. These pressure modules may be placed before and/or after other modules. The pressure modules may comprise any suitable module capable of increasing or decreasing the pressure of the gas stream. In particular embodiments, the pressure module is a compressor. The compressor is capable of increasing the pressure of the gas stream to a value that is suitable for the transferring of the gas stream. In particular embodiments, the pressure module is a valve. The valve is capable of decreasing the pressure of the gas stream to a value that is suitable for the transferring of the gas stream.

FIG. 1 shows a system for selectively filtering constituents from a gas stream, the system comprises a hydrolysis module 120, an acid gas removal module 130, a deoxygenation module 140, and a bioreactor 150. The gas stream may be derived from any industrial, producer, and/or synthesis gas source 110. The gas stream is fed from the industrial, producer, and/or synthesis gas source 110, via a conduit 112, to the hydrolysis module 120 for conversion of at least one constituent in the gas stream, to provide a post-hydrolysis gas stream. The post-hydrolysis gas stream is delivered, via a conduit 122, to the acid gas removal module 130. The acid gas removal module 130 removes at least one constituent 134 from the post-hydrolysis gas stream to produce an acid gas depleted gas stream. The acid gas depleted stream is delivered, via a conduit 132, to the deoxygenation module 140. The deoxygenation module 140 removes at least one constituent 144 from the acid gas depleted stream to produce a post-deoxygenation gas stream. At least a portion of the post-deoxygenation gas stream may be passed, via a conduit 142, to the bioreactor 150 for fermentation. Preferably, the bioreactor contains C1-fixing microorganisms capable of producing products 154 and a post-fermentation gaseous substrate from the gas stream.

At least a portion of the post-fermentation gaseous substrate may be passed back to one or more removal module. In certain instances, the post-fermentation gaseous substrate is passed, via a conduit 152, to the hydrolysis module 120 for conversion of one or more constituent in the post-fermentation gaseous substrate. In certain instances, the post-fermentation gaseous substrate may be stored in a carbon capture means.

Surprisingly, the inventors have identified that by configuring the various modules in a particular sequence that the gas stream provided to the bioreactor 150 comprises a predetermined level of constituents to be fermented by C1-fixing microorganisms without significantly consuming desired compounds and without producing additional inhibitory compounds. It was found that the hydrolysis module 120 was capable of converting at least a portion of the carbonyl sulfide (COS) present in the gas stream to hydrogen sulfide ($H_2S$). It was also found that at least one or more of the constituents removed by the acid gas removal module 130 include carbon dioxide ($CO_2$), and hydrogen sulfide ($H_2S$). By placing the hydrolysis module 120 prior to the acid gas removal module 130, at least a portion of the carbonyl sulfide (COS) converted to hydrogen sulfide ($H_2S$) can be removed from the gas stream by the acid gas removal module 130.

Figure 2:
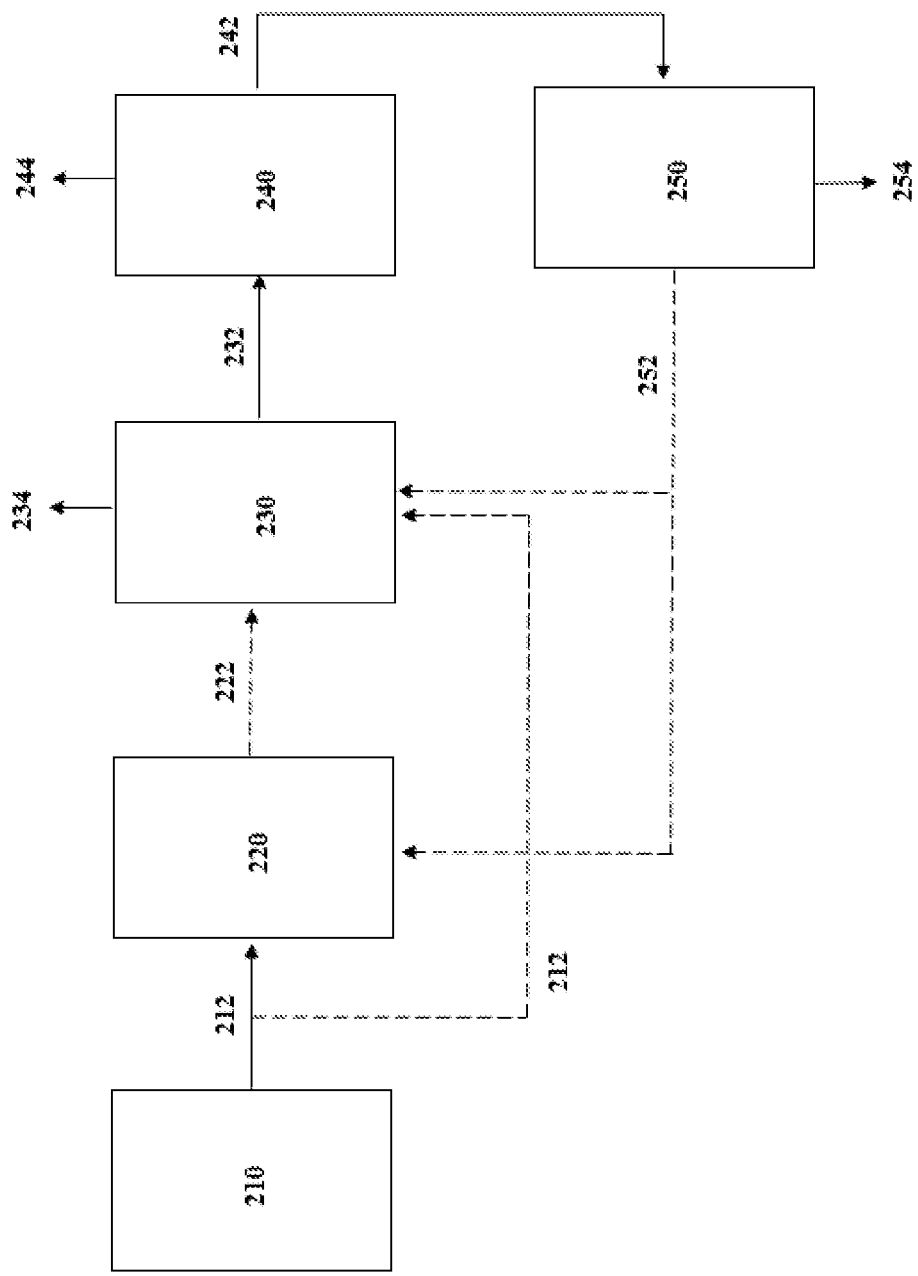
FIG. 2 shows a process integration scheme depicting the bypassing of the hydrolysis module, in accordance with one aspect of the invention.

Additionally, it was found that various modules may not be necessary due to the constituent level present in the gas stream. FIG. 2 shows a system for selectively filtering constituents from a gas stream where the gas stream is capable of bypassing the hydrolysis module 220. In particular embodiments, the level of constituents can be effectively removed without being passed through particular modules. In certain instances, the hydrolysis module 220 is bypassed. When the hydrolysis module 220 is bypassed, the gas stream from the industrial, producer and/or synthesis gas source 210 is fed, via a conduit 212, to the acid gas removal module 230. The acid gas removal module 230 removes at least one constituent 234 from the gas stream to produce an acid gas depleted stream. The acid gas depleted stream is delivered, via a conduit 232, to the deoxygenation module 240. The deoxygenation module 240 removes at least one constituent 244 from the acid gas depleted stream to produce a post-deoxygenation gas stream. At least a portion of the post-deoxygenation gas stream may be passed, via a conduit 242, to the bioreactor 250 for fermentation. Preferably, the bioreactor contains C1-fixing microorganisms capable of producing products 254 and a post fermentation gaseous substrate from the gas stream.

At least a portion of the post-fermentation gaseous substrate may be passed back to one or more removal module. In certain instances, the post-fermentation gaseous substrate is passed, via a conduit 252, to the hydrolysis module 220 for conversion of one or more constituent in the post-fermentation gaseous substrate. In embodiments bypassing the hydrolysis module 220, the post-fermentation gaseous substrate may be passed, via a conduit 252, to the acid gas removal module 230 for removal of at least one constituent 234 from the post-fermentation gaseous substrate. In certain instances, the post-fermentation gaseous substrate may be stored in a carbon capture means.

Figure 3:
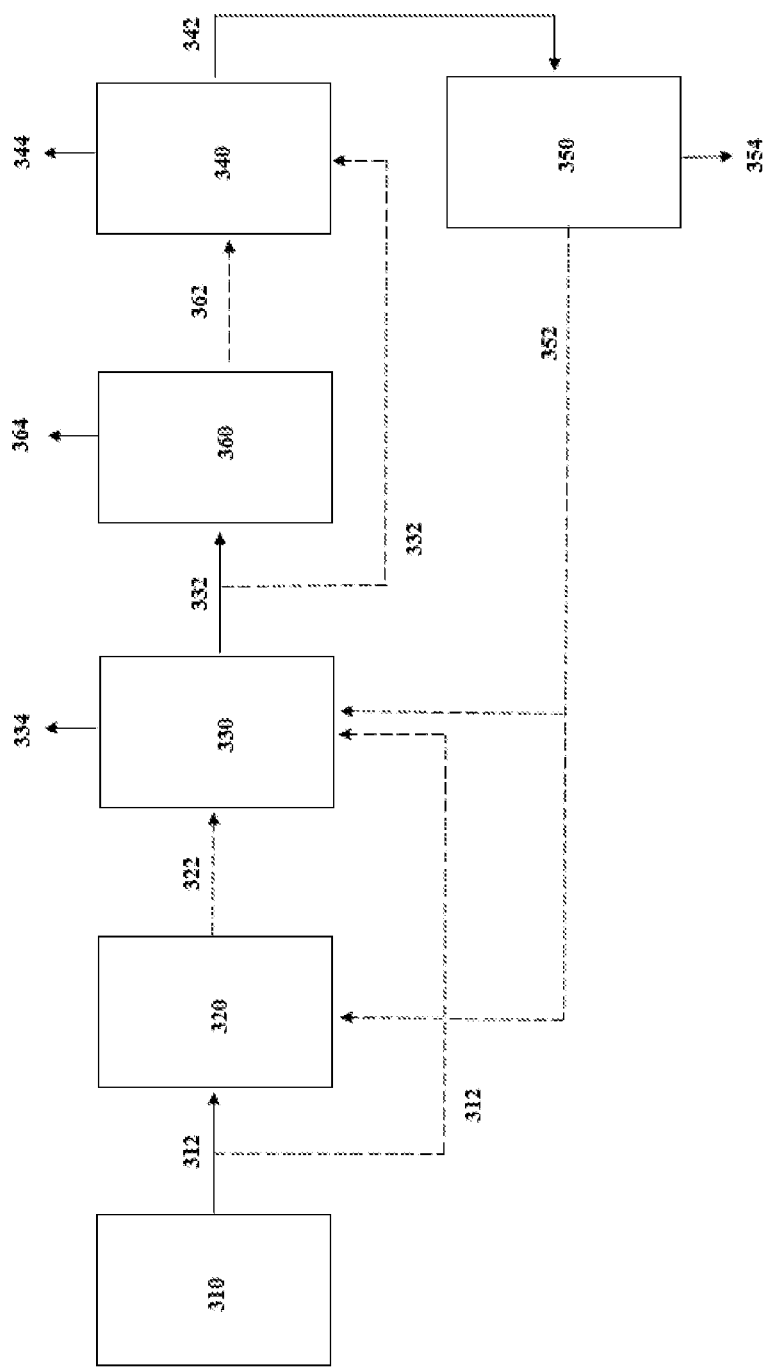
FIG. 3 shows a process integration scheme further including a catalytic hydrogenation module and bypassing functions, in accordance with one aspect of the invention.

Certain gas streams have constituent levels that may require additional modules. FIG. 3 shows a system for selectively filtering constituents from a gas stream, further including a catalytic hydrogenation module 360 prior to the deoxygenation module 340. When the system includes a catalytic hydrogenation module 360, the gas stream is fed from the industrial, producer, and/or synthesis gas source 310, via a conduit 312, to the hydrolysis module 320 for conversion of at least one constituent in the gas stream, to provide a post-hydrolysis gas stream. The post-hydrolysis gas stream is delivered, via a conduit 322, to the acid gas removal module 330. The acid gas removal module 330 removes at least one constituent 334 from the post-hydrolysis gas stream to produce an acid gas depleted stream. The acid gas depleted stream is delivered, via a conduit 332, to the catalytic hydrogenation module 360. The catalytic hydrogenation module 360 removes at least one constituent 364 from the acid gas depleted stream. The acid gas depleted stream is passed from the catalytic hydrogenation module 360 to the deoxygenation module 340, via a conduit 362. The deoxygenation module 340 removes at least one constituent 344 from the gas stream to produce a post-hydrogenation gas stream. At least a portion of the post-hydrogenation gas stream may be passed, via a conduit 342, to the bioreactor 350 for fermentation. Preferably, the bioreactor contains C1-fixing microorganisms capable of producing products 354 and a post-fermentation gaseous substrate from the gas stream.

In particular embodiments, the hydrolysis module 320, catalytic hydrogenation module 360, or both, may be bypassed. When the hydrolysis module 320 and the catalytic hydrogenation module 360 are bypassed, the gas stream from the industrial, producer, and/or synthesis gas source 310 is fed, via a conduit 312, to the acid gas removal module 330. The acid gas removal module 330 removes at least one constituent 334 from the gas stream to produce an acid gas depleted stream. The acid gas depleted stream is delivered, via a conduit 332, to the deoxygenation module 340. The deoxygenation module 340 removes at least one constituent 344 from the acid gas depleted stream to produce a post-deoxygenation gas stream. At least a portion of the post-deoxygenation gas stream may be passed, via a conduit 342, to the bioreactor 350 for fermentation. In particular embodiments, the catalytic hydrogenation module 360 is bypassed while the hydrolysis module 320 is utilized. In certain instances, the catalytic hydrogenation module 360 is utilized while the hydrolysis module 320 is bypassed.

At least a portion of the post-fermentation gaseous substrate may be passed back to one or more removal module. In certain instances, the post-fermentation gaseous substrate is passed, via a conduit 352, to the hydrolysis module 320 for conversion of one or more constituent in the post-fermentation gaseous substrate. In embodiments bypassing the hydrolysis module 320, the post-fermentation gaseous substrate may be passed, via a conduit 352, to the acid gas removal module 330 for removal of at least one constituent 334 from the post-fermentation gaseous substrate. In certain instances, the post-fermentation gaseous substrate may be stored in a carbon capture means.

The system may have further modules selected from the group comprising: particulate removal module, chloride removal module, tar removal module, hydrogen cyanide removal module, additional acid gas removal module, temperature module, and pressure module. These modules may be necessary in order to condition the gas stream between modules, and/or effectively reduce constituent levels to acceptable levels.

Figure 4:
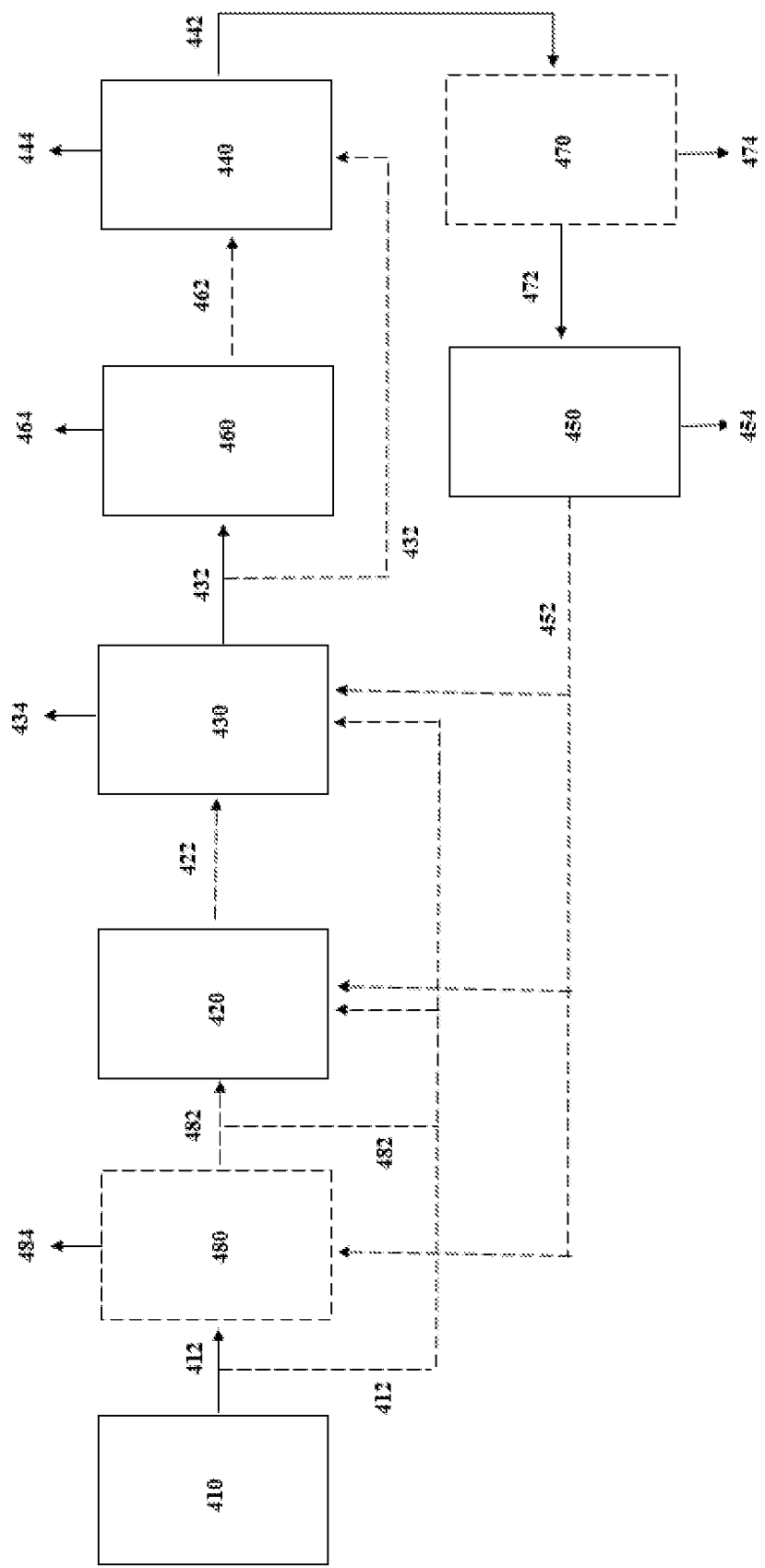
FIG. 4 shows a process integration scheme further including one or more additional module and bypassing functions, in accordance with one aspect of the invention.

FIG. 4 shows a system for selectively filtering constituents from a gas stream, including further modules in the system. In particular embodiments, one or more module may be placed after the deoxygenation module 440. When the system includes one or more module after the deoxygenation module 440, the gas stream is passed from the industrial, producer, and/or synthesis gas source 410, via a conduit 412, to the hydrolysis module 420 for conversion of at least one constituent in the gas stream, to provide a post-hydrolysis gas stream. The post-hydrolysis gas stream is delivered, via a conduit 422, to the acid gas removal module 430. The acid gas removal module 430 removes at least one constituent 434 from the post-hydrolysis gas stream to produce an acid gas depleted stream. The acid gas depleted stream is delivered, via a conduit 432, to the catalytic hydrogenation module 460 for removal of at least one constituent 464 from the gas stream. The gas stream is then fed, via a conduit 462, from the catalytic hydrogenation module 460 to the deoxygenation module 440. The deoxygenation module 440 removes at least one constituent 444 from the gas stream. The gas stream is fed, via a conduit 442, from the deoxygenation module 440 to one or more further module 470. The one or more further module 470 removes and/or converts at least one constituent 474 in the gas stream. At least a portion of the gas stream from the one or more further module 470 may be passed, via a conduit 472, to the bioreactor 450 for fermentation. Preferably, the bioreactor contains C1-fixing microorganisms capable of producing products 454 and a post-fermentation gaseous substrate from the gas stream. In particular embodiments, the one or more further module 470 is a hydrogen cyanide removal module and/or an additional acid gas removal module.

In particular embodiments, one or more further module 480 may be placed before the hydrolysis module 420. When the system includes one or more module before the hydrolysis module 420, the gas stream is passed from the industrial, producer, and/or synthesis gas source 410, via a conduit 412, to the one or more further module 480. The one or more further module 480 removes and/or converts at least one constituent 484 in the gas stream. The gas stream is then fed, via a conduit 482, to the hydrolysis module 420 for further processing. In embodiments bypassing the hydrolysis module 420, the gas stream may be fed via the conduit 482 to the acid gas removal module 430. In particular embodiments, the system may include one or more further module 480 before the hydrolysis module 420 and one or more further module 470 after the deoxygenation module 440.

At least a portion of the post-fermentation gaseous substrate may be passed back to one or more removal module. In certain instances, the post-fermentation gaseous substrate is passed, via a conduit 452, to the hydrolysis module 420 for conversion of one or more constituent in the post-fermentation gaseous substrate. In embodiments bypassing the hydrolysis module 420, the post-fermentation gaseous substrate may be passed, via a conduit 452, to the acid gas removal module 430 for removal of at least one constituent 434 from the post-fermentation gaseous substrate. In embodiments incorporating one or more module before the hydrolysis module 420, the post-fermentation gaseous substrate may be passed, via a conduit 452, to the one or more further module 480. In certain instances, the post-fermentation gaseous substrate may be stored in a carbon capture means.

Preferably, the gas stream is capable of being fermented by one or more C1-fixing microorganism. The C1-fixing microorganism is typically a carboxydotrophic bacterium. In particular embodiments, the carboxydotrophic bacterium is selected from the group comprising *Moorella, Clostridium, Ruminococcus, Acetobacterium, Eubacterium, Butyribacterium, Oxobacter, Methanosarcina, Methanosarcina,* and *Desulfotomaculum*. In various embodiments, the carboxydotrophic bacterium is *Clostridium autoethanogenum*.

The following examples are set forth as representative of the present invention. These examples are not to be construed as limiting the scope of the invention, as these and other equivalent embodiments will be apparent in view of the present disclosure and appended claims.

Example 1

A gas cleaning system was configured to receive a blended gas stream. The blended gas stream being designed to represent a stream received from a steel mill. The gas cleaning system incorporated the following modules in the following order: (i) hydrolysis module, (ii) acid gas removal module, (iii) catalytic hydrogenation module, and (iv) deoxygenation module. The hydrolysis module consisting of a bed of gamma-alumina adsorbent (BASF F-200). The acid gas removal module consisting of a bed of zinc oxide adsorbent (RCI ZOP-116). The catalytic hydrogenation module consisting of palladium on alumina catalyst (BASF RO-20/47). The deoxygenation module consisting of a copper catalyst (BASF CU0226S).

Prior to testing the substrate, the hydrogenation catalyst was reduced in 1% $H_2$ in $N_2$ at 120° C. for at least 12 hours. The deoxygenation catalyst was reduced in 1% $H_2$ in $N_2$ at 250° C. for at least 12 hours The composition of the blended gas stream being fed to the gas cleaning system is illustrated by the below table.

| Compound | |
|---|---|
| Hydrogen | 6.8% |
| Carbon Monoxide | 30.6% |
| Carbon Dioxide | 18.4% |
| Nitrogen | 43.0% |
| Water | 4500 ppm |
| Oxygen | 6700 ppm |
| Acetylene | 500 ppm |
| Hydrogen Cyanide | 60 ppm |

In addition to the above compounds, trace levels of methane and dimethyl ether were detected in the blended stream. These compounds are impurities in the feed gas.

These rate at which the gas stream was fed and the inlet temperature of each module is illustrated by the below table. The pressure of each bed was 345 kPag.

| Module | Gas Hourly Space Velocity (GHSV) Hour$^{-1}$ | Module Inlet Temperature (° C.) |
|---|---|---|
| Hydrolysis | 2000 | 200 |
| Acid Gas Removal | 370 | 20 |
| Catalytic Hydrogenation | 5500 | 120 |
| Deoxygenation | 4000 | 200 |

This configuration successfully produced a fermentable gas stream. Target contaminant removal was achieved. The composition of the fermentable gas stream is illustrated by the below table.

| Compound | |
|---|---|
| Oxygen | 0.50 ppm |
| Acetylene | 0.062 ppm |
| Hydrogen Cyanide | <0.010 ppm |

Trace amounts of methane were detected in the fermentable gas stream. However, the amount of methane in the outlet stream was similar to the amount of methane detected in the inlet stream, thus no production of methane was detected. Trace ethane and ethylene were detected. Ethane and ethylene are products from acetylene removal and are not microbe inhibitors. No other impurities were detected in the outlet stream using this configuration. No microbe inhibitors were formed using this configuration.

The outlet concentration of the CO was 30.1%. This outlet concentration corresponds to 2.6% consumption of the input CO, which is well below the maximum preferable consumption of 10%.

Example 2

A gas cleaning system, similar to Example 1, was configured to receive a blended gas stream. The blended gas stream being designed to represent a stream received from a steel mill. The gas cleaning system incorporated the following modules in the following order: (i) hydrolysis module, (ii) acid gas removal module, and (iii) deoxygenation module. The hydrolysis module consisting of a bed of gamma-alumina adsorbent (BASF F-200). The acid gas removal module consisting of a bed of zinc oxide adsorbent (RCI ZOP-116). The deoxygenation module consisting of a copper catalyst (BASF CU0226S).

The composition of the blended gas stream being fed to the gas cleaning system is illustrated by the below table.

| Compound | |
|---|---|
| Hydrogen | 6.8% |
| Carbon Monoxide | 30.6% |
| Carbon Dioxide | 18.4% |
| Nitrogen | 43.0% |
| Water | 4500 ppm |
| Oxygen | 6700 ppm |
| Acetylene | 500 ppm |
| Hydrogen Cyanide | 60 ppm |

In addition to the above compounds, trace levels of methane were detected in the blended stream. These compounds are impurities in the feed gas.

These rate at which the gas stream was fed and the inlet temperature of each module is illustrated by the below table. The pressure of each bed was 345 kPag.

| Module | Gas Hourly Space Velocity (GHSV) Hour$^{-1}$ | Module Inlet Temperature (° C.) |
|---|---|---|
| Hydrolysis | 2000 | 200 |
| Acid Gas Removal | 370 | 20 |
| Deoxygenation | 4000 | 200 |

This configuration successfully produced a fermentable gas stream. Target contaminant removal was achieved. The composition of the fermentable gas stream is illustrated by the below table.

| Compound | |
|---|---|
| Oxygen | 0.45 ppm |
| Acetylene | 0.065 ppm |
| Hydrogen Cyanide | <0.010 ppm |

Trace amounts of methane were detected in the fermentable gas stream. However, the amount of methane in the outlet stream was similar to the amount of methane detected in the inlet stream, thus no production of methane was detected. Trace ethane and ethylene were detected. Ethane and ethylene are products from acetylene removal. Trace amounts of dimethyl ether and acetaldehyde were detected. Dimethyl ether and acetaldehyde are not microbe inhibitors. No microbe inhibitors were formed using this configuration.

Trace amounts of dimethyl ether and acetaldehyde were removed by passing the fermentable gas stream to an organic compound removal module. The flowrate of the gas stream to the organic compound removal module was such that the gas hourly space velocity was 370 hr.$^{-1}$.

The outlet concentration of the CO was 29.8%. This outlet concentration corresponds to 4.0% consumption of the input CO, which is well below the maximum preferable consumption of 10%.

In addition to running the gas cleaning system at 345 KPag, using this configuration and this gas composition, the inventors increased the pressure such that the pressure of each bed was 690 kPag in order to evaluate how pressure may affect the system.

It was found that at increased pressure (690 kPag for each bed), the configuration successfully produced a fermentable gas stream. Target contaminant removal was achieved. The composition of the fermentable gas stream is illustrated by the below table.

| Compound | | |
|---|---|---|
| Oxygen | 0.41 | ppm |
| Acetylene | 0.076 | ppm |
| Hydrogen Cyanide | <0.010 | ppm |

Trace amounts of methane were detected in the fermentable gas stream. However, the amount of methane in the outlet stream was similar to the amount of methane detected in the inlet stream, thus no production of methane was detected. Trace ethane and ethylene were detected. Ethane and ethylene are products from acetylene removal and are not microbe inhibitors. Trace amounts of dimethyl ether and acetaldehyde were detected. Dimethyl ether and acetaldehyde are not microbe inhibitors. No impurities were detected in the outlet stream using this configuration.

Trace amounts of dimethyl ether and acetaldehyde were removed by passing the fermentable gas stream to an organic compound removal module. The flowrate of the gas stream to the organic compound removal module was such that the gas hourly space velocity was 370 hr.$^{-1}$.

The outlet concentration of the CO was 29.8%. This outlet concentration corresponds to 3.3% consumption of the input CO, which is well below the maximum preferable consumption of 10%.

Example 3

A gas cleaning system was configured to receive a blended gas stream. The blended gas stream being designed to represent a stream received from a steel mill. The gas cleaning system incorporated the following modules in the following order: (i) hydrolysis module, (ii) acid gas removal module, (iii) catalytic hydrogenation module, (iv) deoxygenation module, and (v) organic compound removal module. The hydrolysis module consisting of a bed of gamma-alumina adsorbent (BASF F-200). The acid gas removal module consisting of a bed of zinc oxide adsorbent (RCI ZOP-116). The catalytic hydrogenation module consisting of palladium on alumina catalyst (BASF RO-20/47). The deoxygenation module consisting of a copper catalyst (BASF Cu 0226S).

Prior to testing the substrate, the hydrogenation catalyst was reduced in 1% $H_2$ in $N_2$ at 120° C. for at least 12 hours. The deoxygenation catalyst was reduced in 1% $H_2$ in $N_2$ at 250° C. for at least 12 hours The composition of the blended gas stream being fed to the gas cleaning system is illustrated by the below table.

| Compound | |
|---|---|
| Hydrogen | 6.2% |
| Carbon Monoxide | 27.6% |
| Carbon Dioxide | 16.2% |

| Compound | | |
|---|---|---|
| Nitrogen | 49.1% | |
| Water | 2400 | ppm |
| Hydrogen Sulfide | 40.0 | ppm |
| Carbonyl Sulfide | 4.0 | ppm |
| Oxygen | 6000 | ppm |
| Acetylene | 550 | ppm |
| Hydrogen Cyanide | 20 | ppm |

In addition to the above compounds, trace levels of methane were detected in the blended stream. These compounds are impurities in the feed gas.

These rate at which the gas stream was fed and the inlet temperature of each module is illustrated by the below table. The pressure of each bed was 690 kPag.

| Module | Gas Hourly Space Velocity (GHSV) Hour$^{-1}$ | Module Inlet Temperature (° C.) |
|---|---|---|
| Hydrolysis | 2000 | 200 |
| Acid Gas Removal | 370 | 20 |
| Catalytic Hydrogenation | 5500 | 120 |
| Deoxygenation | 4000 | 200 |
| Organic Removal | 370 | 20 |

This configuration successfully produced a fermentable gas stream. Target contaminant removal was achieved. The composition of the fermentable gas stream is illustrated by the below table.

| Compound | | |
|---|---|---|
| Oxygen | 0.38 | ppm |
| Acetylene | 0.168 | ppm |
| Hydrogen Cyanide | <0.030 | ppm |

Trace amounts of methane were detected in the fermentable gas stream. However, the amount of methane in the outlet stream was similar to the amount of methane detected as an impurity in the inlet stream, thus no production of methane was detected. Trace ethane and ethylene were detected. Ethane and ethylene are products from acetylene removal and are not microbial inhibitors. No other impurities were detected in the outlet stream using this configuration. No microbial inhibitors were formed using this configuration of modules.

The outlet concentration of the CO was 26.6%. This outlet concentration corresponds to 3.8% consumption of the input CO, which is well below the maximum preferable consumption of 10%.

Example 4

A gas cleaning system was configured similarly to Example 3 to receive a blended gas stream. The blended gas stream being designed to represent a stream received from a steel mill. The gas cleaning system incorporated the following modules in the following order: (i) hydrolysis module, (ii) acid gas removal module, (iii) deoxygenation module, and (iv) organic compound removal module. The hydrolysis module consisting of a bed of gamma-alumina adsorbent (BASF F-200). The acid gas removal module consisting of a bed of zinc oxide adsorbent (RCI ZOP-116). The deoxygenation module consisting of a copper catalyst (BASF Cu 0226S).

The composition of the blended gas stream being fed to the gas cleaning system is illustrated by the below table.

| Compound | |
|---|---|
| Hydrogen | 6.2% |
| Carbon Monoxide | 27.6% |
| Carbon Dioxide | 16.2% |
| Nitrogen | 49.1% |
| Water | 2400 ppm |
| Hydrogen Sulfide | 40.0 ppm |
| Carbonyl Sulfide | 4.0 ppm |
| Oxygen | 6000 ppm |
| Acetylene | 550 ppm |
| Hydrogen Cyanide | 20 ppm |

In addition to the above compounds, trace levels of methane were detected in the blended stream. These compounds are impurities in the feed gas.

These rate at which the gas stream was fed and the inlet temperature of each module is illustrated by the below table. The pressure of each bed was 690 kPag.

| Module | Gas Hourly Space Velocity (GHSV) Hour$^{-1}$ | Module Inlet Temperature (° C.) |
|---|---|---|
| Hydrolysis | 2000 | 200 |
| Acid Gas Removal | 370 | 20 |
| Deoxygenation | 4000 | 200 |
| Organic Removal | 370 | 20 |

This configuration successfully produced a fermentable gas stream. Target contaminant removal was achieved. The composition of the fermentable gas stream is illustrated by the below table.

| Compound | |
|---|---|
| Oxygen | 0.34 ppm |
| Acetylene | 0.073 ppm |
| Hydrogen Cyanide | <0.010 ppm |

Trace amounts of methane were detected in the fermentable gas stream. However, the amount of methane in the outlet stream was similar to the amount of methane detected as an impurity in the inlet stream, thus no production of methane was detected. Trace ethane and ethylene were detected. Ethane and ethylene are products from acetylene removal and are not microbial inhibitors. No other impurities were detected in the outlet stream using this configuration. No microbial inhibitors were formed using this configuration of modules.

The outlet concentration of the CO was 26.2%. This outlet concentration corresponds to 4.9% consumption of the input CO, which is well below the maximum preferable consumption of 10%.

Example 5

A gas cleaning system, similar to Example 2, was configured to receive a blended gas stream. The blended gas stream has higher concentrations of microbial inhibitors. The concentrations being in the range that is expected from biomass or municipal solid waste gasification or treated coke oven gas. The gas cleaning system incorporated the following modules in the following order: (i) hydrolysis module, (ii) acid gas removal module, (iii) deoxygenation module, and (iv) organic compound removal module. The hydrolysis module consisting of a bed of gamma-alumina adsorbent (BASF F-200). The acid gas removal module consisting of a bed of zinc oxide adsorbent (RCI ZOP-116). The deoxygenation module consisting of a copper catalyst (BASF Cu 0226S).

Prior to testing the substrate, the deoxygenation catalyst was reduced in 1% $H_2$ in $N_2$ at 250° C. for at least 12 hours.

The composition of the blended gas stream being fed to the gas cleaning system is illustrated by the below table.

| Compound | |
|---|---|
| Hydrogen | 4.1% |
| Carbon Monoxide | 17.8% |
| Carbon Dioxide | 10.7% |
| Nitrogen | 66.3% |
| Water | 2000 ppm |
| Oxygen | 7600 ppm |
| Acetylene | 860 ppm |
| Hydrogen Cyanide | 280 ppm |

In addition to the above compounds, trace levels of methane were detected in the blended stream. This compound is an impurity in the feed gas.

These rate at which the gas stream was fed and the inlet temperature of each module is illustrated by the below table. The pressure of each bed was 690 kPag.

| Module | Gas Hourly Space Velocity (GHSV) Hour$^{-1}$ | Module Inlet Temperature (° C.) |
|---|---|---|
| Hydrolysis | 2000 | 200 |
| Acid Gas Removal | 370 | 20 |
| Deoxygenation | 4000 | 200 |
| Organic Removal | 370 | 20 |

This configuration successfully produced a fermentable gas stream. Target contaminant removal was achieved. The composition of the fermentable gas stream is illustrated by the below table.

| Compound | |
|---|---|
| Oxygen | 0.46 ppm |
| Acetylene | 0.040 ppm |
| Hydrogen Cyanide | <0.010 ppm |

Trace amounts of methane were detected in the fermentable gas stream. However, the amount of methane in the outlet stream was similar to the amount of methane detected as an impurity in the inlet stream, thus no production of methane was detected. Trace ethane and ethylene were detected. Ethane and ethylene are products from acetylene removal and are not microbial inhibitors. No other impurities were detected in the outlet stream using this configuration. No microbial inhibitors were formed using this configuration of modules.

The outlet concentration of the CO was 16.6%. This outlet concentration corresponds to 6.8% consumption of the input CO, which is well below the maximum preferable consumption of 10%.

Example 6

A gas cleaning system was configured to receive a blended gas stream. The blended gas stream being designed to represent a stream received from a steel mill. The gas cleaning system incorporated only one module. The module consisted of a copper catalyst (BASF Cu 0226S).

Prior to testing a substrate, the deoxygenation catalyst was reduced in 1% $H_2$ in $N_2$ at 250° C. for at least 12 hrs.

The composition of the blended gas stream being fed to the gas cleaning system is illustrated by the below table.

| Compound | |
|---|---|
| Hydrogen | 7.0% |
| Carbon Monoxide | 31.6% |
| Carbon Dioxide | 18.5% |
| Nitrogen | 41.9% |
| Water | 4500 ppm |
| Oxygen | 5900 ppm |
| Acetylene | 490 ppm |
| Hydrogen Cyanide | 20 ppm |

In addition to the above compounds, trace levels of methane were detected in the blended stream. This compound is an impurity in the feed gas.

The rate at which the gas stream was fed corresponds to a 4000 hr−1 gas hourly space velocity. The inlet temperature of the module was 200° C. The pressure of the module was 690 kPag.

This module successfully produced a fermentable gas stream. Target contaminant removal was achieved. The composition of the fermentable gas stream is illustrated by the below table.

| Compound | |
|---|---|
| Oxygen | 0.41 ppm |
| Acetylene | 0.060 ppm |
| Hydrogen Cyanide | <0.010 ppm |

Trace amounts of methane were detected in the fermentable gas stream. However, the amount of methane in the outlet stream was similar to the amount of methane detected as an impurity in the inlet stream, thus no production of methane was detected. Trace ethane and ethylene were detected. Ethane and ethylene are products from acetylene removal and are not microbial inhibitors. Methanol was detected in the fermentable gas stream. Methanol is not a microbial inhibitor. No other impurities were detected in the outlet stream using this configuration. No microbial inhibitors were formed using this configuration of modules.

The outlet concentration of the CO was 30.2%. This outlet concentration corresponds to 4.2% consumption of the input CO, which is well below the maximum preferable consumption of 10%.

Example 7

A gas cleaning system was configured to receive a blended gas stream. The blended gas stream being designed to represent a stream received from a steel mill. The gas cleaning system incorporated only one module. The module consisted of a copper catalyst (BASF Cu 0226S).

Prior to testing a substrate, the catalyst was reduced in 1% $H_2$ in $N_2$ at 250° C. for at least 12 hrs. Following the catalyst reduction, the catalyst was sulfided using a gas stream of 1% $H_2S$, 5% $H_2$ in $N_2$. The catalyst was sulfided at 220° C. for 18 hours.

The composition of the blended gas stream being fed to the gas cleaning system is illustrated by the below table.

| Compound | |
|---|---|
| Hydrogen | 6.1% |
| Carbon Monoxide | 27.2% |
| Carbon Dioxide | 16.0% |
| Nitrogen | 49.8% |
| Water | 2400 ppm |
| Hydrogen Sulfide | 39 ppm |
| Carbonyl Sulfide | 4.0 ppm |
| Oxygen | 6200 ppm |
| Acetylene | 550 ppm |
| Hydrogen Cyanide | 19 ppm |

In addition to the above compounds, trace levels of methane were detected in the blended stream. This compound is an impurity in the feed gas.

The rate at which the gas stream was fed corresponds to a 2000 hr−1 gas hourly space velocity. The inlet temperature of the module was 280° C. The pressure of the module was 690 kPag.

This module successfully produced a fermentable gas stream. Target contaminant removal was achieved. The composition of the fermentable gas stream is illustrated by the below table.

| Compound | |
|---|---|
| Oxygen | 0.42 ppm |
| Acetylene | 0.581 ppm |
| Hydrogen Cyanide | 0.011 ppm |

Trace amounts of methane were detected in the fermentable gas stream. However, the amount of methane in the outlet stream was similar to the amount of methane detected as an impurity in the inlet stream, thus no production of methane was detected. Trace ethane and ethylene were detected. Ethane and ethylene are products from acetylene removal and are not microbial inhibitors. Acetaldehyde was detected in the fermentable gas stream. Acetaldehyde is not a microbial inhibitor. No other impurities were detected in the outlet stream using this configuration. No microbial inhibitors were formed using this configuration of modules.

The outlet concentration of the CO was 26.9%. This outlet concentration corresponds to 1.0% consumption of the input CO, which is well below the maximum preferable consumption of 10%.

Example 8

A gas cleaning system similar to Example 7 was configured to receive a blended gas stream. The blended gas stream comprised higher concentrations of microbial inhibitors. The concentrations being in the range expected from biomass or municipal solid waste gasification or treated coke oven gas. The gas cleaning system incorporated only one module. The module consisted of a copper catalyst (BASF Cu 0226S).

The composition of the blended gas stream being fed to the gas cleaning system is illustrated by the below table.

| Compound | |
|---|---|
| Hydrogen | 3.8% |
| Carbon Monoxide | 16.4% |
| Carbon Dioxide | 9.1% |
| Nitrogen | 69.6% |
| Water | 2200 ppm |
| Hydrogen Sulfide | 40 ppm |
| Carbonyl Sulfide | 4 ppm |
| Oxygen | 6600 ppm |
| Acetylene | 1060 ppm |
| Hydrogen Cyanide | 400 ppm |

In addition to the above compounds, trace levels of methane were detected in the blended stream. This compound is an impurity in the feed gas.

The rate at which the gas stream was fed corresponds to a 1000 hr−1 gas hourly space velocity. The inlet temperature of the module was 300° C. The pressure of the module was 690 kPag.

This module successfully produced a fermentable gas stream. Target contaminant removal was achieved. The composition of the fermentable gas stream is illustrated by the below table.

| Compound | |
|---|---|
| Oxygen | 3.1 ppm |
| Acetylene | 0.960 ppm |
| Hydrogen Cyanide | 0.280 ppm |

Trace amounts of methane were detected in the fermentable gas stream. However, the amount of methane in the outlet stream was similar to the amount of methane detected as an impurity in the inlet stream, thus no production of methane was detected. Trace ethane and ethylene were detected. Ethane and ethylene are products from acetylene removal and are not microbial inhibitors. Acetaldehyde was detected in the fermentable gas stream. Acetaldehyde is not a microbial inhibitor. No other impurities were detected in the outlet stream using this configuration. No microbial inhibitors were formed using this configuration of modules.

The outlet concentration of the CO was 15.9%. This outlet concentration corresponds to 3.0% consumption of the input CO, which is well below the maximum preferable consumption of 10%.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgment that that prior art forms part of the common general knowledge in the field of endeavor in any country.

The use of the terms "a" and "an" and "the" and similar referents in the context of describing the invention (especially in the context of the following claims) are to be construed to cover both the singular and the plural unless otherwise indicated herein or clearly contradicted by context. The terms "comprising," "having," "including," and "containing" are to be construed as open-ended terms (i.e., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (i.e., "or") should be understood to mean either one, both, or any combination thereof of the alternatives. As used herein, the term "about" means±20% of the indicated range, value, or structure, unless otherwise indicated.

Recitation of ranges of values herein is merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (i.e., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for removing constituents from an input gas stream, comprising contacting the input gas stream with a catalyst to produce a fermentable gas stream, wherein the fermentable gas stream comprises less than 100 ppm oxygen, less than 1 ppm acetylene, and less than 1 ppm hydrogen cyanide, and wherein the catalyst comprises reduced metal copper supported on alumina, silica, titania, ceria, lanthana, carbon, silica-alumina, or zeolites.

2. The process of claim 1, further comprising passing at least a portion of the fermentable gas stream to a bioreactor, wherein the bioreactor contains a culture comprising a fermentation broth and one or more microorganisms.

3. The process of claim 2 wherein at least one microorganism is a carboxydotrophic bacterium.

4. The process of claim 3 wherein the carboxydotrophic bacterium may be selected from *Moorella, Clostridium*, Ruminococcus, Acetobacterium, *Eubacterium, Butyribacterium, Oxobacter, Methanosarcina, Desulfotomaculum*, or any combination thereof.

5. The process of claim 1 wherein the microorganism is *Clostridium autoethanogenum*.

6. The process of claim 1, wherein at least a portion of the input gas stream is a synthesis gas and/or a producer gas.

7. The process of claim 1, wherein the process further comprises measuring the level of constituents in the input gas stream and/or the fermentable gas stream.

8. The process of claim 1, wherein the input gas stream comprises CO, $CO_2$, $H_2$, or any combination thereof.

9. The process of claim 1, wherein the input gas stream comprises oxygen up to 7000 ppm, acetylene up to 700 ppm, and hydrogen cyanide up to 60 ppm.

10. The process of claim 1, wherein the input gas stream comprises oxygen up to 10000 ppm, acetylene up to 1500 ppm, and hydrogen cyanide up to 500 ppm.

11. The process of claim 1, wherein the input gas stream comprises carbon monoxide and the process consumes less than 10 percent of the carbon monoxide in the input gas stream.

12. The process of claim 1, wherein the process is carried out at a pressure of at least 138 kPag.

13. The process of claim 1, wherein the catalyst is copper (I) or sulfided copper (I) supported on alumina.

14. The process of claim 1, wherein the catalyst is copper (II) or sulfided copper (II) supported on alumina.

15. The process of claim 1 wherein the input gas stream comprises mercury, the fermentable gas stream comprises less mercury than the input gas stream, and the copper is sulfided.

16. The process of claim 1, wherein the input gas stream comprises oxygen up to 10000 ppm, acetylene up to 1500 ppm, and hydrogen cyanide up to 500 ppm.

17. An apparatus comprising:
a. a vessel having a vessel gas inlet and a vessel fermentable gas outlet wherein the vessel contains catalyst comprising copper supported on alumina, silica, titania, ceria, lanthana, carbon, silica-alumina, or zeolites wherein the copper is reduced metal copper or the catalyst is sulfided; and
b. a bioreactor having a bioreactor gas inlet in fluid communication with the vessel fermentable gas outlet and a bioreactor fermentation broth output wherein the bioreactor comprises at least one C1-fixing microorganism.

18. The apparatus of claim 17 further comprising at least one monitoring device in communication with the vessel gas inlet, the vessel fermentable gas outlet, or both.

19. A process for removing constituents from an input gas stream, comprising contacting the input gas stream with a catalyst to produce a fermentable gas stream, wherein the fermentable gas stream comprises less than 100 ppm oxygen, less than 1 ppm acetylene, and less than 1 ppm hydrogen cyanide, and wherein the catalyst comprises copper supported on alumina, silica, titania, ceria, lanthana, carbon, silica-alumina, or zeolites and wherein the catalyst is sulfided.

20. The process of claim 19 wherein the input gas stream comprises mercury and the fermentable gas stream comprises less mercury than the input gas stream.

* * * * *